United States Patent [19]

Sźantay et al.

[11] 4,424,224

[45] Jan. 3, 1984

[54] APOVINCAMINOL DERIVATIVE AND COMPOSITIONS AND METHODS UTILIZING IT FOR TREATING PSORIASIS

[75] Inventors: Csaba Sźantay; Lajos Szabó; György Kalaus; Zsuzsanna Gyulai; Mária Zájer née Balázs; Lilla Forgách; Egon Karpati; Arpád Kiraly; Gyóngyvér Kiraly nee Soos; László Szporny; Bela Rosdy, all of Budapest, Hungary

[73] Assignee: Richter Gedeon Vegyészeti Gyár Rt, Budapest, Hungary

[21] Appl. No.: 345,632

[22] Filed: Feb. 4, 1982

[30] Foreign Application Priority Data

Feb. 11, 1981 [HU] Hungary .................................... 322

[51] Int. Cl.$^3$ .................. A61K 31/435; C07D 461/00

[52] U.S. Cl. ....................................... 424/256; 546/51

[58] Field of Search .......................... 424/256; 546/51

[56] References Cited

U.S. PATENT DOCUMENTS 4,065,458 12/1977 Lorincz et al. .................... 546/153
4,328,231 5/1982 Zajer nee Balazs et al. ....... 424/256

FOREIGN PATENT DOCUMENTS 2462909 2/1981 France .

OTHER PUBLICATIONS

Lorincz et al., Chemical Abstracts, vol. 82, 129279v (1975).

*Arzneimittel Forschung,* vol. 26, No. 10, Rosdy et al., pp. 1923–1926 (1976).

*Primary Examiner*—Diana G. Rivers

*Attorney, Agent, or Firm*—Karl F. Ross; Herbert Dubno

[57] ABSTRACT

The invention relates to the new apovincaminol-3′,4′,5′-trimethoxy-benzoate and acid addition salts thereof.

The new compound may be prepared by reacting apovincaminol or an acid addition salt thereof with 3,4,5-trimethoxy benzoic acid or a reactive derivative thereof capable of acylation and if desired converting the compound thus obtained into an acid addition salt.

The new compound of the present invention can be used in therapy in the treatment of skin diseases attached to pathological cell proliferation and in the propylaxis of such diseases.

6 Claims, No Drawings

APOVINCAMINOL DERIVATIVE AND COMPOSITIONS AND METHODS UTILIZING IT FOR TREATING PSORIASIS

This invention relates to a new apovincaminol derivative and acid addition salts of the same, a process for the preparation thereof and pharmaceutical compositions containing the same.

According to an aspect of the present invention there is provided the new apovincaminol-3',4',5'-trimethoxy-benzoate and acid addition salts thereof.

The acid addition salts of the apovincaminol-3',4',5'-trimethoxy-benzoate may be formed with inorganic or organic acids. From the salts formed with inorganic acids the hydrochlorides, sulfates and phosphates, while from the salts formed with organic acids the hydrogen tartarates, succinates, citrates and ascorbinates are particularly useful.

It is known that the apovincaminol and its acetate exhibit an effect on the coronary artery (French Patent Specification No. 2 035 784). It is also known that the apovincaminol benzoate possesses general vasodilatory properties (Hungarian Patent Specification No. 166 476; CA 82, 129 279 v [1975]) and the esters of apovincaminol formed with alkane carboxylic acid having 3-12 carbon atoms exhibit cerebral vasodilatory effect (Hungarian Patent Specification No. 171 662, the corresponding U.S. Pat. No. 4,108,996 and the German Federal Republic Patent Specification No. 26 32 118.)

Thus all the known esters of apovincaminol exhibit vascular effects. On the other hand the new compound of the present invention inhibits the enzyme activity of phosphodiesterase and can be used first of all in the treatment of skin diseases related to the pathological cell proliferation and in the prophylaxis of the recurrence of such diseases.

Diseases related to the pathological proliferation of the epidermis are relatively frequent and involve a few percent of the population. Such a disease is psoriasis. This disease occurs only on humans.

Since psoriasis does not occur on animals, the activity of the compounds against psoriasis can be made probable in animal tests only in an indirect manner.

Voorhees et al. [Arch. Derm. 104, 359-365, (1971)] have found that the pathological cell proliferation is accompanied by the decrease of the level of cyclic adenozine monophosphate (c-AMP). It is known that c-AMP is formed under the effect of adenyl-cyclase and decomposed by phosphodiesterase. Voorhees succeeded in influencing the psoriasis by agents which stimulate the function of adenyl cyclase (such as norepinephrine) or inhibit the function of phosphodiesterase (e.g. papaverine).

By planning our model experiment test we have started from the presumption that the statement of Voorhees is relevant to the contrary as well. Thus if it can be proven that a compound inhibits the function of phosphodiesterase this makes it probable in an indirect way that the said compound is suitable for the treatment of skin diseases attached to the pathological cell proliferation. Later this presumption turned out to be true: compounds showing phosphodiesterase inhibiting activity in in vitro tests proved to be active in the treatment of psoriasis in clinical experiments as well.

Our model tests are carried out with the aid of phosphodiesterase isolated from animal body tissues (rat brain, bovine brain, bovine heart). The enzyme is isolated according to the method of J. Schröder and H. V. Richenberg [Biochem. Biophys. Acta 302, 50 (1973)], the isolated phosphodiesterase is purified by the method of J. G. Hardman and E. W. Sutherland [J. Biol. Chem. 240, 3704/1965/] and finally the activity of the purified enzyme is measured according to the radioisotop method of G. Pöch in the presence of an excess of tritiated c-AMP (10.1 millimoles of c-AMP substrate, from which the 3H-c-AMP is 2.59 K Bq) in an incubation system at first without an inhibitor agent, and thereafter in the presence of apovincaminol-3',4', 5'-trimethoxy benzoate as inhibitor after an incubation period of 20 minutes [N. S. Arch. Pharmacol. 268, 272 (1971)]. From the test compound a 1 millimolar stock solution is prepared and to the incubated enzyme preparation various amounts are added with the aid of the said stock solution so that the concentration of the test compound in the incubated sample should correspond to $5\times10^{-7}$, $1\times10^{-6}$, $5\times10^{-6}$, $1\times10^{-5}$, $5\times10^{-5}$ and $10^{-4}$ mole/liter, respectively. The aqueous solution of the reference compound (papaverine) is added to the enzyme preparation in a similar manner.

The activity of the control (enzyme solution containing no inhibitor) is taken as 100% and the activity of the solutions containing the apovincaminol-3',4', 5'-trimethoxy benzoate and papaverine is expressed in the percentage of the control. The results measured on the enzyme isolated from rat brain are as follows:

| Test compound (enzyme inhibitor) | Concentrated of the test compound, mole/liter Effect on the enzyme activity, % of the control | | | | |
|---|---|---|---|---|---|
| | $1\times10^{-6}$ | $5\times10^{-6}$ | $1\times10^{-5}$ | $5\times10^{-5}$ | $1\times10^{-4}$ |
| Apovincaminol-3',4',5'-tri-methoxy-benzoate-HCl | 94.0 | 64.5 | 49.2 | 47.2 | 44.8 |
| Papaverine, HCl | | 91.2 | 89.7 | 60.5 | 38.8 |

The results on enzyme isolated from bovine brain and bovine heart are measured in a similar manner. By using the results obtained the enzyme activity is plotted against the logarithm of the enzyme inhibitor concentration (expressed in μmoles). The concentration of the enzyme inhibitor which decreases the enzyme activity by 50% ($I_{50}$) is shown by the curve. The results obtained are summarized in the following Table.

| Test compound | $I_{50}$ values, in μmoles on phosphodiesterase enzyme isolated from | | |
|---|---|---|---|
| | bovine brain | bovine heart | rat brain |
| Apovincaminol-3',4',5'-trimethoxy-benzoate.HCl | 5 | 1.5 | 10 |
| Papaverine.HCl | 90 | 50 | 70 |

It appears from the above Table that on enzyme isolated from bovine brain, bovine heart and rat brain the compound of the present invention is 18, 33 and 7 times, respectively, more active than the papaverine used as reference compound.

The first clinical tests were carried out with topical compositions containing the active ingredient (ointment, cream, solution, tincture, paste, aerosol). Creams containing 2%, 1%, 0.5%, 0.25% and 0.1% of apovincaminol-3',4',5'-trimethoxy-benzoate respectively, were used.

Patients suffering from psoriasis were used. A further fundamental point of view of the selection was that the patients did not receive simultaneously a systemic treatment of their basic disease (e.g. an immune supressive, cytostatical or glucocorticoidal treatment).

Groups consisting of five patients each were examined by the so-called plaque method. One side of the symmetrical skin lesions was treated with the cream containing the active ingredient while the other side was treated with a placebo. The other affected skin surfaces of the patient were treated by other topical methods—among others with an ointment generally used for the treatment of psoriasis, containing flumethasone pivalate and salicylic acid—said ointment being used as reference substance.

The test had been started with a cream having a higher active ingredient content and further patients were treated with a cream having the lowest active ingredient content but being still active. The cream was spread on the skin surface twice or three times a day until the symptoms disappeared or improved (generally 1–6 weeks).

The effect was evaluated by observing three different symptoms—inflammation, infiltration and desquamation (peeling). The intensity of the symptoms was expressed by the following scale between 0 and 3:

0=no symptoms
1=moderate symptom
2=strong symptom
3=very strong symptom

The symptoms were evaluated before treatment (I), after a treatment of seven days (II) and after treatment of fourteen days (III). In the following Table the average number of points (total number of points multiplied by the number of patients) is disclosed. A 2% cream is used.

| | Average number of points | | | | | | | | |
|---|---|---|---|---|---|---|---|---|---|
| | Infiltration | | | Inflammation | | | Desquamation | | |
| Test compound | I | II | III | I | II | III | I | II | III |
| Apovincaminol-3',4',5'-trimethoxy-benzoate | 1.8 | 0.6 | 0.5 | 1.8 | 1.3 | 0.75 | 1.2 | 0.4 | 0 |

The above tests prove unambiguously that the compositions of the present invention can be successfully used in the therapy of psoriasis. During the treatment no undesired side effects were observed.

According to a further feature of the present invention there is provided a process for the preparation of the new apovincaminol-3',4',5'-trimethoxy-benzoate and acid addition salts thereof which comprises reacting apovincaminol or an acid addition salt thereof with 3,4,5-trimethoxy-benzoic acid or a reactive derivative thereof capable of acylation and if desired converting the compound thus obtained into an acid addition salt thereof.

The process of the present invention is carried out preferably in the presence of an organic solvent, particularly a chlorinated hydrocarbon or an aliphatic ketone or pyridine, particularly in methylene chloride, chloroform or acetone. If a 3,4,5-trimethoxy-benzoyl halide is used as acylating agent, the reaction is carried out in the presence of an equimolar amount or a small excess of an acid binding agent. For this purpose e.g. an alkali carbonate, alkali hydrogen carbonate or organic amine may be used. If 3,4,5-trimethoxy-benzoic acid is used as acylating agent the reaction is carried out in the presence of a catalytic amount of an acid (preferably hydrochloric acid or sulfuric acid) or an activator of the carboxylic group and/or a dehydrating agent. The carboxylic group may be activated by a halogenated phenol, preferably pentachlors phenol. As dehydrating agent, e.g. N,N'-dicyclohexyl carbodiimide may be used. The acylation may be carried out at a temperature between −20° C. and the boiling point of the reaction mixture, preferably at 20°-60° C.

The desired product may be isolated from the reaction mixture by extraction and/or evaporation.

The product thus obtained may be converted into a pharmaceutically acceptable acid addition salt. Salt formation may be carried out by using an inorganic or organic acid (e.g. hydrochloric acid, sulfuric acid or phosphoric acid or tartaric acid, succinic acid, citric acid or ascorbic acid). The salt formation is carried out by methods known per se. One may proceed preferably by adding a solution of the acid in ethyl ether or acetone to the solution of the base. Salt formation is accomplished at a pH value of 3–6.

According to a still further feature of the present invention there are provided pharmaceutical compositions having phosphodiesterase inhibiting effect and being mainly useful in the treatment of skin diseases attached to pathological cell proliferation and the prophylaxis of the recurrence of such diseases, the said compositions comprising as active ingredient apovincaminol-3',4',5'-trimethoxy-benzoate or a pharmaceutically acceptable acid additions salt thereof and optionally further therapeutically active compounds in admixture with usual pharmaceutical carriers and/or diluents.

The active ingredient content of the pharmaceutical compositions of the present invention is preferably 0.1–8.0%, particularly 0.2–2.0%. The compositions may optionally contain further therapeutically active compounds, such as antibiotics, cytostatical agents, prostaglandins, ditranol, salicylic acid, tar, antiinflammatory agents, immunosupressants, glucocorticoids and—in the case of compositions suitable for parenteral administration—local anaesthesia agents. The glucocorticoide may preferably be triamcindonacetamide. The active ingredient may be finished preferably in the form of compositions for topical external use, such as creams, ointments, solutions, gelees, aerosols, aerosol foams, adhesive plasters etc.

The active ingredient may be preferably used in the form of the base but acid addition salts—e.g. tartarate—may be applied as well.

It is preferred to incorporate the active ingredient into a cream, which can be washed off.

The creams may be prepared by dissolving the active ingredient in a solvent of the alcohol type, preferably in propylene glycol or ethylene glycol or a mixture thereof formed with a small amount of water, and admixing the solution thus obtained with a readily spreadable fatty phase being consistent with the skin.

The said fatty phase may comprise cetyl alcohol, stearyl alcohol, cetostearyl alcohol, paraffin oil, glycerine monostearate etc.

The cream may also contain an emulsifying agent—preferably polyoxyethylene sorbitan monooleate or monostearate—and a preservative such as benzoic acid derivatives, preferably methyl-p-hydroxy benzoate.

The creams may contain preferably 0.25–2.0% of the active ingredient 45–50% of glycole, 23–27% of paraffin oil, 11–15% of stearyl alcohol and optionally up to 100% other auxiliary agents.

The active ingredient can also be finished in the form of an ointment which can not be washed off with water by incorporating the active ingredient directly in the fatty phase.

The active ingredient can also be finished in the form of a solution which may contain e.g. 20–40% of propylene glycol or dipropylene glycole, 40–55% of 96% ethanol and up to 100% of distilled water.

The aerosol formulations may be prepared by adding to the solution of the active ingredient in propylene glycol a fatty substance—e.g. isopropyl myristate—and a propellant (e.g. freon).

An aerosol foam may be prepared by adding the alcoholic solution of the active ingredient to a mixture of 0.5–1.5% of cetostearyl alcohol, 1–3% benzyl alcohol, 15–20% of polyoxyethylene monooleate or monostearate and 25–30% of water and thereafter adding a propellant (such as freon).

Injectable solutions suitable for parenteral administration preferably applicable in a subcutaneous or intracutaneous route may be prepared by dissolving a salt of the active ingredient in a 0.72% aqueous sodium chloride solution and adjusting the pH of the solution to 5.

The pharmaceutical compositions of the present invention can be prepared by methods of the pharmaceutical industry known per se. One may proceed by admixing the active ingredient and optionally further therapeutically active compounds with suitable inert nontoxic usual pharmaceutical carriers and/or additives and finishing the mixture thus obtained in a form suitable for medical use.

Further details of the present invention can be found in the following Examples without limiting the scope of protection to the said Examples.

EXAMPLE 1

Preparation of (−)-apovincaminol-3′,4′,5′-trimethoxy-benzoate 3.10 g (10.1 millimoles) of (−)-apovincaminol are dissolved in 60 ml of anhydrous dichlormethane, whereupon 3.10 g of anhydrous sodium carbonate and 2.50 g (10.9 millimoles) of 3,4,5-trimethoxy-benzoyl chloride are added and the reaction mixture is stirred at room temperature for 24 hours. The reaction mixture is diluted with 100 ml of water, the organic phase is separated and the aqueous layer is extracted twice with 20 ml of dichloromethane each. The united dichloromethane phases are dried over magnesium sulfate, filtered and the filtrate is evaporated in vacuo. Thus 4.50 g of the title compound are obtained, yield 89.1%

Empirical formula $C_{30}H_{34}N_2O_5$.

Molecular weight 502.61.

IR spectrum (film): $\nu_{mas}$ 1725 $cm^{-1}$ (·C═O); 1620 $cm^{-1}$ (═C═C═).

$^1$H-NMR spectrum (deuterochloroform):
δ1.01(t, 3H, $\underline{CH_3}CH_2$·);
3.72(s, 6H, 2×·$OCH_3$);
3.85(s, 3H, ·$OCH_3$);
4.25(s, 1H, anellation);
5.29(s, 1H, ·CH═);
5.4(m, 2H, ·$OCH_2$·);
7.0–7.8(m, 6H, aromatic).

MS (m/e): 502(53), 432(100), 290(17), 261(41), 220(19), 216(23), 212(18), 195(35).

$[\alpha]_D^{25} = -22.0°$ (c=0.7; dichloromethane).

EXAMPLE 2

Preparation of (−)-apovincaminol-3′,4′,5′-trimethoxy-benzoate

The compound prepared according to Example 1 is dissolved in diethyl ether. To the solution a saturated solution of D-tartaric acid in diethyl ether is added until the precipitation of the hydrogen tatarate salt becomes complete. The salt is filtered off and dried. Mp.: 120–121° C. IR spectrum KBr: $\nu_{max}$1730 $cm^{-1}$(−C═0); 1640–1665 $cm^{-1}$(═C═C═). $[\alpha]_D^{25} = -8.5°$ (c=1, pyridine).

Molecular weight 652.7.

EXAMPLE 3

A cream having the following composition is prepared:

| Component | Anount, g |
|---|---|
| Apovincaminol-3′,4′,5′-trimethoxy-benzoate | 2 |
| Propylene glycol | 50 |
| Paraffin oil | 26 |
| Polyethylene glycol | 5 |
| Stearyl alcohol | 15 |
| Glycerol monostearate | 2 |

The active ingredient is dissolved in propylene glycole on a water bath (bath temperature not exceeding 50° C.). The other components are heated until they melt and thereafter cooled to 40°–45° C. under constant stirring. To the melt the solution of the active ingredient is added under stirring and the cream thus obtained is cooled under stirring.

In an analogous manner creams containing 0.25%, 0.5%, 1.0%, and 1.5% of the active ingredient, respectively, are prepared.

EXAMPLE 4

A cream having the following composition is prepared:

| Component | Amount, g |
|---|---|
| Apovincaminol-3′,4′,5′-trimethoxy-benzoate | 2 |
| Triamcinolon acetonide | 0.1 |
| Glycerol monostearate | 3.0 |
| Polyethylene glycol 400 | 5.0 |
| Stearyl alcohol | 13.0 |
| Paraffin oil | 24.9 |
| Propylene glycol | 53.0 |

One proceeds in an analogous manner to Example 3 except that two active ingredients are dissolved in propylene glycol.

EXAMPLE 5

A tincture solution having the following composition is prepared:

| Component | Amount, % |
|---|---|
| Apovincaminol-3',4',5'-trimethoxy-benzoate hydrogen tartarate | 1 |
| Propylene glycol | 30 |
| 96% ethanol | 47 |
| Distilled water | 22 |

EXAMPLE 6

An aerosol having the following composition is prepared:

| Component | Amount, % |
|---|---|
| Apovincaminol-3',4',5'-trimethoxy-benzoate hydrogen tartarate | 0.5 |
| Propylene glycol | 30.0 |
| Isopropyl myristate | 4.5 |
| Freon | 65.0 |

EXAMPLE 7

An aerosol foam having the following composition is prepared:

-continued

| Component | Amount, % |
|---|---|
| Apovincaminol-3',4',5'-trimethoxy-benzoate hydrogen tartarate | 2 |
| Cetostearyl alcohol | 1 |
| Benzyl alcohol | 2 |
| Polyoxyethylene-sorbitan-monostearate | 15 |
| 96% ethanol | 30 |
| Distilled water | 30 |
| Freon | 20 |

What we claim is:

1. Apovincaminol-3',4', 5'-trimethoxy-benzoate and acid addition salts thereof.

2. An anti-psoriasis composition for the treatment of said disease and for the prophylaxis of the recurrence of such disease which comprises a pharmaceutically effective amount of apovincaminol-3',4', 5'-trimethoxy-benzoate or a pharmaceutically acceptable acid addition salt thereof in admixture with a pharmaceutically acceptable inert carrier or auxiliary agent.

3. The anti-psoriasis composition defined in claim 2 which comprises 0.1 to 8.0% of apovincaminol-3', 4', 5'-trimethoxy-benzoate or a pharmaceutically acceptable acid addition salt thereof.

4. The anti-psoriasis composition defined in claim 2 which comprises 0.2 to 2.0% of apovincaminol-3',4',5'-trimethoxy-benzoate or a pharmaceutically acceptable acid addition salt thereof.

5. The anti-psoriasis composition defined in claim 2 in the form of a cream, ointment, solution, aerosol, aerosol foam, or in injectable form suitable for subcutaneous or intracutaneous administration.

6. A method for the treatment or prophylaxis of psoriasis which comprises the step of treating the skin surface with a pharmaceutically effective amount of the anti-psoriasis composition defined in claim 2.

* * * * *